(12) United States Patent
Lee et al.

(10) Patent No.: US 10,130,647 B2
(45) Date of Patent: Nov. 20, 2018

(54) USE OF GINSENOSIDE M1 FOR PREVENTING OR TREATING SILICOSIS

(71) Applicant: WELLHEAD BIOLOGICAL TECHNOLOGY CORP., Taoyuan (TW)

(72) Inventors: Sheau-Long Lee, Taoyuan (TW); Yu-Chieh Lee, Taoyuan (TW); Kuo-Feng Hua, I-Lan (TW)

(73) Assignee: SHEAU-LONG LEE, Taoyuan (TW)

( * ) Notice: Subject to any disclaimer, the term of this patent is extended or adjusted under 35 U.S.C. 154(b) by 0 days.

(21) Appl. No.: 15/558,881

(22) PCT Filed: Mar. 17, 2016

(86) PCT No.: PCT/CN2016/076635
§ 371 (c)(1),
(2) Date: Sep. 15, 2017

(87) PCT Pub. No.: WO2016/146079
PCT Pub. Date: Sep. 22, 2016

(65) Prior Publication Data
US 2018/0064741 A1     Mar. 8, 2018

Related U.S. Application Data

(60) Provisional application No. 62/134,236, filed on Mar. 17, 2015.

(51) Int. Cl.
*A61K 31/704* (2006.01)
*A61K 31/7032* (2006.01)

(52) U.S. Cl.
CPC ........ *A61K 31/704* (2013.01); *A61K 31/7032* (2013.01)

(58) Field of Classification Search
None
See application file for complete search history.

(56) References Cited

U.S. PATENT DOCUMENTS

| | | | |
|---|---|---|---|
| 7,354,941 B2 * | 4/2008 | Marfat | A61K 45/06 514/350 |
| 2004/0087615 A1 * | 5/2004 | Dombroski | C07D 471/04 514/303 |
| 2005/0014816 A1 * | 1/2005 | Compere | C07D 333/38 514/444 |

* cited by examiner

*Primary Examiner* — Traviss C McIntosh, III
(74) *Attorney, Agent, or Firm* — Birch, Stewart, Kolasch & Birch, LLP (57) ABSTRACT

The present invention discloses a new use of ginsenoside M1 for treating or preventing silicosis.

4 Claims, 12 Drawing Sheets

USE OF GINSENOSIDE M1 FOR PREVENTING OR TREATING SILICOSIS

CROSS REFERENCE TO RELATED APPLICATIONS

This application is the National Phase of PCT International Application No. PCT/CN2016/076635, filed on Mar. 17, 2016, which claims priority under 35 U.S.C. 119(e) to U.S. Provisional Application Ser. No. 62/134,236, filed on Mar. 17, 2015, all of which are hereby expressly incorporated by reference into the present application.

FIELD OF THE INVENTION

The present invention relates to a new use of ginsenoside M1 for treating or preventing silicosis.

BACKGROUND OF THE INVENTION

Silicosis is a type of lung disease that is caused by inhaling silica particles, usually from working in mines and quarries and in some other occupations such as construction, foundry-work, ceramics and glass-making. Silica particles affects lung's normal function. The symptoms include shortness of breath, severe cough and weakness.

Ginsenosides, the main active ingredients of ginseng, are known to have a variety of pharmacological activities, e.g. antitumor, antifatique, antiallergic and antioxidant activities. Ginsenosides share a basic structure, composed of gonane steroid nucleus having 17 carbon atoms arranged in four rings. Ginsenosides are metalized in the body, and a number of recent studies suggest that ginsenoside metabolites, rather than naturally occurring ginsenosides, are readily absorbed in the body and act as the active components. Among them, ginsenoside M1 is known as one metabolite of protopanaxadiol-type ginsenosides via the gypenoside pathway by human gut bacteria. Until now, no prior art references report the effect of ginsenoside M1 in treatment of silicosis.

BRIEF SUMMARY OF THE INVENTION

In the present invention, it is unexpected found that ginsenoside M1 is effective in alleviating or delaying onset or progression of silicosis. Therefore, the present invention provides a new approach for treatment or prevention of silicosis in a subject.

In particular, the present invention provides a method for treating silicosis in a subject in need thereof comprising administering to the subject an amount of ginsenoside M1 effective to treat the subject.

Specifically, the method treating of the present invention is effective in inhibiting silica crystal-induced activation of NLRP3 inflammasome. More specifically, the method of treating of the present invention is effective in inhibiting silica crystal-induced interleukin 1β production through NLRP3 inflammasome.

In some embodiments, ginsenoside M1 is administered by parenteral or enteral route.

The present invention also provides use of ginsenoside M1 in manufacturing a medicament for treatment of silicosis in a subject in need.

The details of one or more embodiments of the invention are set forth in the description below. Other features or advantages of the present invention will be apparent from the following detailed description of several embodiments, and also from the appending claims.

BRIEF DESCRIPTION OF THE DRAWINGS

For the purpose of illustrating the invention, there are shown in the drawings embodiments. It should be understood, however, that the invention is not limited to the preferred embodiments shown. In the drawings.

DETAILED DESCRIPTION OF THE INVENTION

Unless defined otherwise, all technical and scientific terms used herein have the meaning commonly understood by a person skilled in the art to which this invention belongs. As used herein, the following terms have the meanings ascribed to them unless specified otherwise.

The articles "a" and "an" are used herein to refer to one or more than one (i.e., at least one) of the grammatical object of the article. By way of example, "an element" means one element or more than one element.

IL-1β is one of the important cytokines rapidly synthesized in an inactive immature form (precursor of IL-1β, proIL-1β) via transcriptional activation in lipopolysaccharide (LPS)-activated macrophages (Hsu and Wen, 2002). Unlike that of other cytokines, secretion of mature IL-1β requires processing of its precursor form proIL-1β by caspase-1, a cysteine protease (Miller et al., 1997). IL-1β release is controlled by caspase-1-containing multi-protein complexes called NLRP3 inflammasome, which controls caspase-1 activity and IL-1β release (Cassel et al., 2011; Jin and Flavell, 2010). Full activation of the NLRP3 inflammasome requires both a priming signal from LPS-stimulated TLR4 and an activation signal from a second stimulus, e.g. silica crystals and alum crystals, the former controlling the expression of NLRP3 and proIL-1β and the latter controlling caspase-1 activation (Martinon et al., 2009; Schroder and Tschopp, 2010; Davis et al., 2011; Cassel et al., 2011; Jin and Flavell, 2010). A strong link between the NLRP3 inflammasome and the development of inflammatory disease is becoming increasingly evident. Crystalline silica, also known as silicon dioxide ($SiO_2$), is found in nature as sand or quartz. While ingestion of silica is harmless and non-toxic, inhalation of small silica crystals can lead to acute lung inflammation. Chronic silica exposure can lead to the development of pneumoconiosis silicosis, an irreversible, fibrotic pulmonary disease. Recent reports have revealed that silica crystals induce release of mature IL-1β through activating the NALP3 inflammasome (Hornung et al., 2008; Peeters et al., 2014). Silicosis is characterized by rapid neutrophil influx into lung and massive production of IL-1β (Huaux, 2007). A pronounced lung infiltration of neutrophils was detected in wild-type mice exposed to silica crystals, which was absent in IL-1R-deficient silica crystal exposed mice (Hornung et al., 2008). Inhibition of silica crystals-induced NLRP3 inflammsome activation and IL-1β production prevents and mitigates silicosis.

In the present invention, it is unexpectedly found that ginsenoside M1 can reduce silica crystal-induced IL-1β production (FIG. 1) and LPS-induced NLRP3 and proIL-1β expression (FIG. 2) in macrophages. These results indicate that ginsenoside M1 can prevent and mitigate silicosis.

Therefore, the present invention provides a method for treating silicosis in a subject in need thereof comprising administering to the subject an amount of ginsenoside M1 effective to treat the subject. The present invention also provides use of ginsenoside M1 in manufacturing a medicament for treatment of silicosis in a subject in need.

Particular, the method of treating is effective in inhibiting silica crystal-induced activation of NLRP3 inflammasome. More particularly, the method of treating is effective in inhibiting silica crystal-induced IL-1β production through NLRP3 inflammasome.

Ginsenoside M1, 20-O-β-D-glucopyranosyl-20(S)-protopanaxadiol, is one of saponin metabolites known in the art. The chemical structure of ginsenoside M1 is as follows:

Ginsenoside M1 is known as one metabolite of protopanaxadiol-type ginsenosides via the gypenoside pathway by human gut bacteria. Ginsenoside M1 can be found in blood or urine after intake. Ginsenoside M1 may be prepared from ginseng plants through fungi fermentation by methods known in the art, such as Taiwan Patent Application No. 094116005 (1280982) and U.S. Pat. No. 7,932,057, the entire content of which is incorporated herein by reference. In certain embodiments, the ginseng plants for preparing the ginsenoside M1 include Araliaceae family, *Panax* genus, e.g. *P. ginseng* and *P. pseudo-ginseng* (also named Sanqi). In general, the method of preparation of ginsenoside M1 includes the steps of (a) providing powder of ginseng plant materials (e.g. leaves or stems); (b) providing a fungus for fermenting the ginseng plant materials, wherein the fermentation temperature is ranged from 20-50° C., the fermentation humidity is ranged from 70-100%, the pH value is ranged from 4.0-6.0, and the fermentation period is ranged from 5-15 days; (c) extracting and collecting the fermentation products; and (d) isolating 20-O-β-D-glucopyranosyl-20(S)-protopanaxadiol from the fermentation products.

When ginsenoside M1 is described as "isolated" or "purified" in the present invention, it should be understood as not absolutely isolated or purified, but relatively isolated or purified. For example, purified ginsenoside M1 refers to one that is more purified compared to its naturally existing form. In one embodiment, a preparation comprising purified ginsenoside M1 may comprise ginsenoside M1 in an amount of more than 50%, more than 60%, more than 70%, more than 80%, more than 90%, or 100% (w/w) of the total preparation. It should be understood that when a certain number was used herein to show a ratio or dosage, said number generally includes that within the range of 10% more and less, or more specifically, the scope of 5% more and less than the number.

The term "individual" or "subject" used herein includes human and non-human animals such as companion animals (such as dogs, cats and the like), farm animals (such as cows, sheep, pigs, horses and the like), or laboratory animals (such as rats, mice, guinea pigs and the like).

The term "treating" as used herein refers to the application or administration of a composition including one or more active agents to a subject afflicted with a disorder, a symptom or conditions of the disorder, a progression of the disorder or at risk of developing the disorder, with the purpose to cure, heal, alleviate, relieve, alter, remedy, ameliorate, improve, or affect the disorder, the symptoms or conditions of the disorder, the disabilities induced by the disorder, or the onset or progression of the disorder.

The term "therapeutically effective amount" used herein refers to the amount of an active ingredient to confer a therapeutic effect in a treated subject. For example, an effective amount for treating silicosis is an amount that can inhibit silica crystal-induced activation of NLRP3 inflammasome, more particularly, an amount that can inhibit silica crystal-induced interleukin 1β production through NLRP3 inflammasome.

The therapeutically effective amount may change depending on various reasons, such as administration route and frequency, body weight and species of the individual receiving said pharmaceutical, and purpose of administration. Persons skilled in the art may determine the dosage in each case based on the disclosure herein, established methods, and their own experience. For example, in certain embodiments, the oral dosage of ginsenoside M1 used in the present invention is 10 to 1,000 mg/kg daily. In some examples, the oral the oral dosage of ginsenoside M1 used in the present invention is 100 to 300 mg/kg daily, 50 to 150 mg/kg daily, 25 to 100 mg/kg daily, 10 to 50 mg/kg daily, or 5 to 30 mg/kg daily. In addition, in some embodiments of the invention, ginsenoside M1 is administered periodically for a certain period of time, for example, daily administration for at least 15 days, one month or two months or longer.

According to the present invention, ginsenoside M1 may be used as an active ingredient for treating silicosis. In one embodiment, a therapeutically effective amount of the active ingredient may be formulated with a pharmaceutically acceptable carrier into a pharmaceutical composition of an appropriate form for the purpose of delivery and absorption. Depending on the mode of administration, the pharmaceutical composition of the present invention preferably comprises about 0.1% by weight to about 100% by weight of the active ingredient, wherein the percentage by weight is calculated based on the weight of the whole composition.

As used herein, "pharmaceutically acceptable" means that the carrier is compatible with the active ingredient in the composition, and preferably can stabilize said active ingredient and is safe to the individual receiving the treatment. Said carrier may be a diluent, vehicle, excipient, or matrix to the active ingredient. Some examples of appropriate excipients include lactose, dextrose, sucrose, sorbose, mannose, starch, Arabic gum, calcium phosphate, alginates, tragacanth gum, gelatin, calcium silicate, microcrystalline cellulose, polyvinyl pyrrolidone, cellulose, sterilized water, syrup, and methylcellulose. The composition may additionally comprise lubricants, such as talc, magnesium stearate, and mineral oil; wetting agents; emulsifying and suspending agents; preservatives, such as methyl and propyl hydroxybenzoates; sweeteners; and flavoring agents. The composition of the present invention can provide the effect of rapid, continued, or delayed release of the active ingredient after administration to the patient.

According to the present invention, the form of said composition may be tablets, pills, powder, lozenges, packets, troches, elixers, suspensions, lotions, solutions, syrups, soft and hard gelatin capsules, suppositories, sterilized injection fluid, and packaged powder.

The composition of the present invention may be delivered via any physiologically acceptable route, such as oral, parenteral (such as intramuscular, intravenous, subcutaneous, and intraperitoneal), transdermal, suppository, and intranasal methods. Regarding parenteral administration, it is preferably used in the form of a sterile water solution, which may comprise other substances, such as salts or glucose sufficient to make the solution isotonic to blood. The water solution may be appropriately buffered (preferably with a pH value of 3 to 9) as needed. Preparation of an appropriate parenteral composition under sterile conditions may be accomplished with standard pharmacological techniques well known to persons skilled in the art, and no extra creative labor is required.

According to the present invention, ginsenoside M1 or compositions comprising ginsenoside M1 as the active ingredient may be used in treating individuals with silicosis or at risk of silicosis. Specifically, ginsenoside M1 or compositions comprising ginsenoside M1 as the active ingredient may be administered to individuals with silicosis or individuals at the risk of acquiring silicosis, by inhibiting silica crystal-induced activation of NLRP3 inflammasome, so as to prevent occurrence of the disease or improve the symptoms or delay deterioration of the symptoms.

The present invention is further illustrated by the following examples, which are provided for the purpose of demonstration rather than limitation.

EXAMPLE

1. Materials and Methods

Ginsenoside M1, 20-O-β-D-glucopyranosyl-20(S)-protopanaxadiol (named LCHK168 below), was prepared by methods known in the art, such as those described in Taiwan Patent Application No. 094116005 (I280982) and U.S. Pat. No. 7,932,057.

The mouse macrophages cell line J774A.1 and human monocytic leukemia cell line THP-1 was obtained from the American Type Culture Collection (Rockville, Md.) and cultured in RPMI 1640 medium supplemented with 10% heat-inactivated fetal bovine serum (FBS) and 2 mM L-glutamine (all from Life Technologies, Carlsbad, Calif.) at 37° C. in a 5% $CO_2$ incubator. To induce monocyte-to-macrophage differentiation, THP-1 cells were cultured for 48 h in RPMI-1640 medium supplemented with 100 nM phorbol 12-myristate 13-acetate (Sigma-Aldrich).

Figure 1:
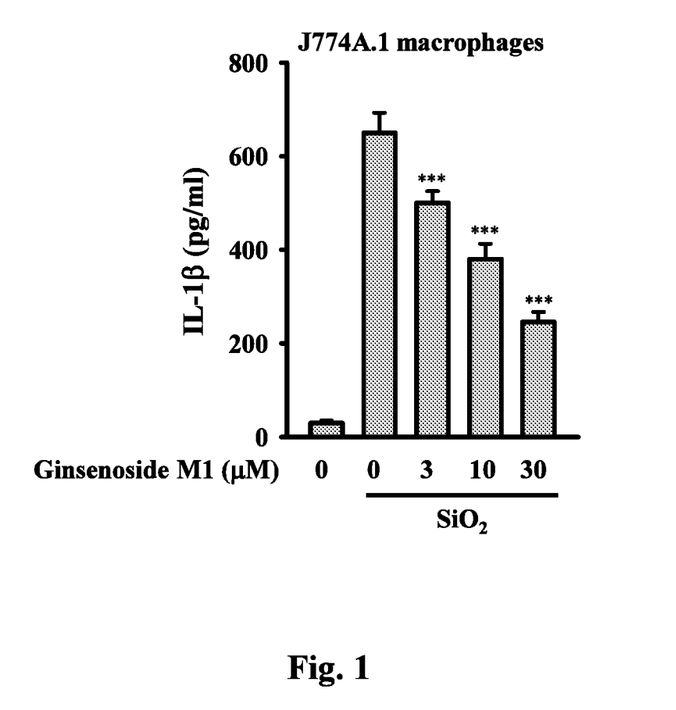
FIG. 1 shows that mouse J774A.1 macrophages were incubated for 30 min with or without Ginsenoside M1, then for 30 min with or without 1 μg/ml LPS in the continued presence or absence of Ginsenoside M1, and then for 24 h with or without 200 μg/ml silica crystal. The levels of IL-1β in the culture medium were measured by ELISA. *** indicates a significant difference at the level of $p<0.001$ compared to MSU alone.

In FIG. 1, J774A.1 macrophages ($1\times10^5$ cells/500 μl medium/well) were incubated for 30 min with or without Ginsenoside M1, then for 2 h with or without 1 μg/ml LPS (from *Escherichia coli* 0111:B4, purchased from Sigma, St. Louis, Mo.) in the continued presence or absence of Ginsenoside M1, and then for 24 h with or without 200 μg/ml silica crystal (purchased from InvivoGen, San Diego, Calif.). The levels of IL-1β in the culture medium were measured by ELISA.

Figure 2:
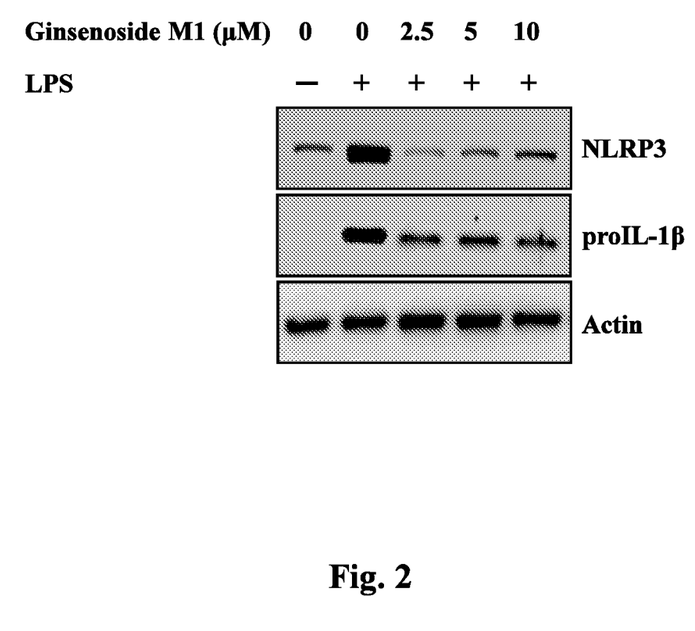
FIG. 2 shows that mouse J774A.1 macrophages were incubated for 30 min with or without Ginsenoside M1, then for 6 h with or without 1 μg/ml LPS in the continued presence or absence of Ginsenoside M1. The levels of NLRP3 and proIL-1μ in the cell lysates were measured by Western blot.

In FIG. 2, J774A.1 macrophages ($2\times10^6$ cells/2 ml medium/dish) were incubated for 30 min with or without Ginsenoside M1, then for 6 h with or without 1 μg/ml LPS in the continued presence or absence of Ginsenoside M1. The levels of NLRP3 and proIL-1β in the cell lysates were measured by Western blot. In brief, After treatment, the cells were collected and lysed at 4° C. in lysis buffer (25 mM Tris-HCl, pH 7.5, 100 mM NaCl, 2.5 mM EDTA, 2.5 mM EGTA, 20 mM NaF, 1 mM $Na_3VO_4$, 20 mM sodium β-glycerophosphate, 10 mM sodium pyrophosphate, 0.5% Triton X-100) containing protease inhibitor cocktail (Sigma, St. Louis, Mo.), then the whole cell lysate was separated by SDS-PAGE and electrotransferred to a PVDF membrane. The membranes were incubated for 1 h at room temperature in blocking solution (5% nonfat milk in phosphate buffered saline with 0.1% Tween 20), then were incubated for 2 h at room temperature with NLRP3 or proIL-1β antibody in blocking solution. After three washes in PBS with 0.1% Tween 20, the membrane was incubated for 1 h at room temperature with HRP-conjugated secondary antibody in blocking buffer and developed using an enhanced chemiluminescence Western blot detection system.

Figure 3:
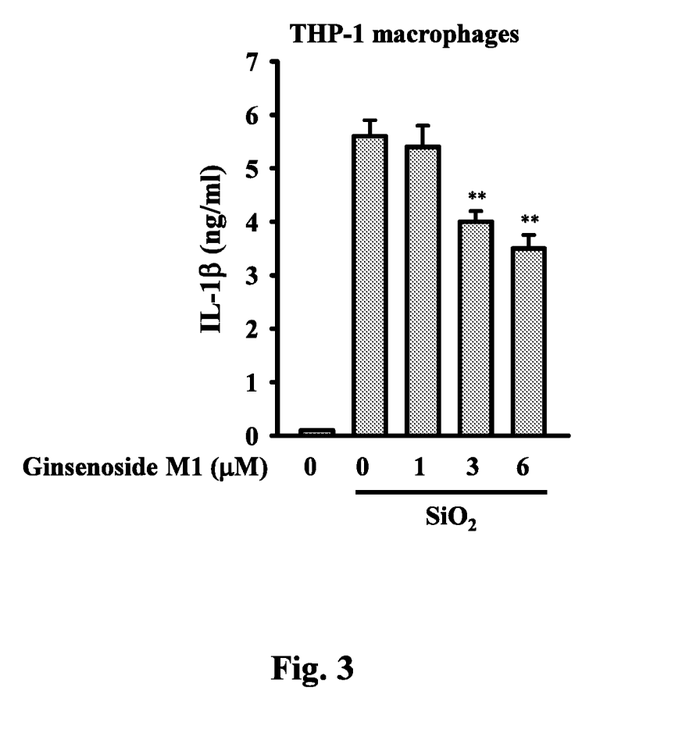
FIG. 3 shows that THP-1 macrophages ($1\times10^5$ cells/500 μl medium/well) were incubated for 30 min with or without Ginsenoside M1, then for 5 h with or without 1 μg/ml LPS in the continued presence or absence of Ginsenoside M1, and then for 24 h with or without 200 μg/ml silica crystal. The levels of IL-1β in the culture medium were measured by ELISA. ** indicates a significant difference at the level of $p<0.01$ compared to silica crystal alone.
Figure 4:
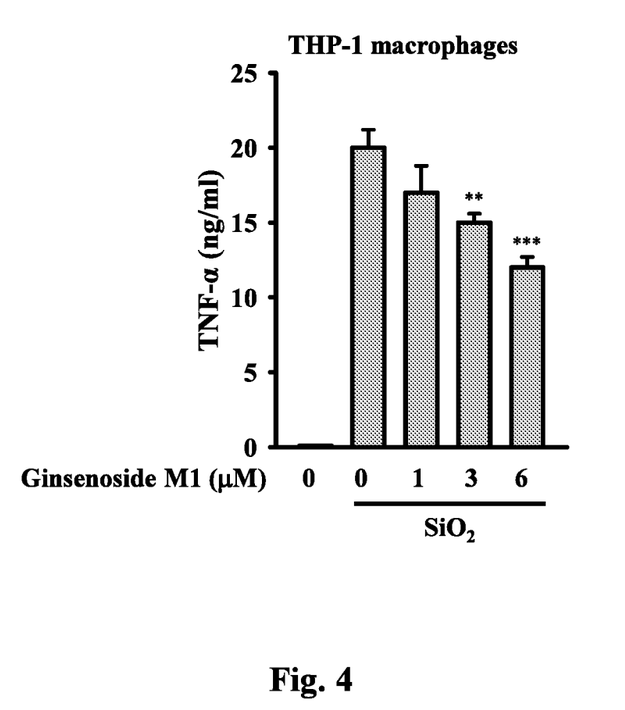
FIG. 4 shows that THP-1 macrophages ($1\times10^5$ cells/500 μl medium/well) were incubated for 30 min with or without Ginsenoside M1, then for 5 h with or without 1 μg/ml LPS in the continued presence or absence of Ginsenoside M1, and then for 24 h with or without 200 μg/ml silica crystal. The levels of TNF-α in the culture medium were measured by ELISA.  and * indicates a significant difference at the level of $p<0.01$ and $p<0.001$, respectively compared to silica crystal alone.
Figure 5:
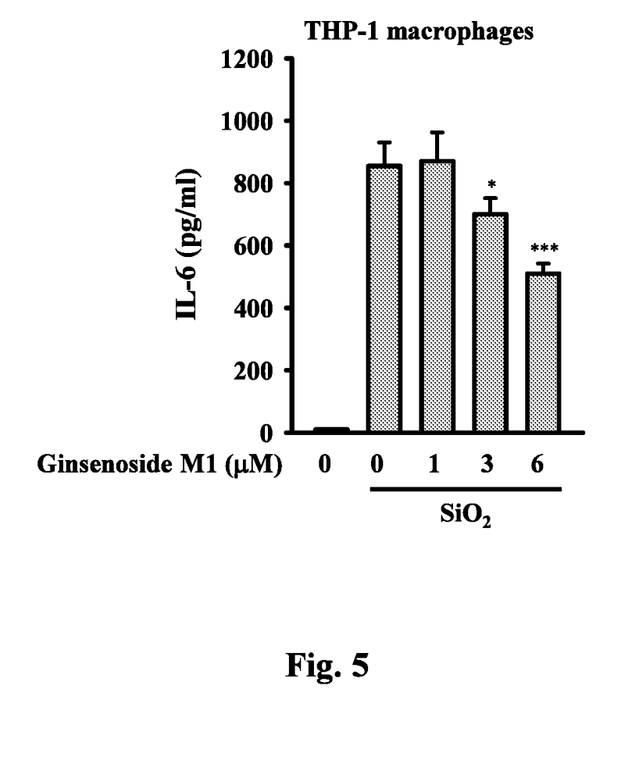
FIG. 5 shows that THP-1 macrophages ($1\times10^5$ cells/500 μl medium/well) were incubated for 30 min with or without Ginsenoside M1, then for 5 h with or without 1 μg/ml LPS in the continued presence or absence of Ginsenoside M1, and then for 24 h with or without 200 μg/ml silica crystal. The levels of IL-6 in the culture medium were measured by ELISA. * and *** indicates a significant difference at the level of $p<0.05$ and $p<0.001$, respectively compared to silica crystal alone.

In FIG. 3-5, THP-1 macrophages ($1\times10^5$ cells/500 μl medium/well) were incubated for 30 min with or without Ginsenoside M1, then for 5 h with or without 1 μg/ml LPS in the continued presence or absence of Ginsenoside M1, and then for 24 h with or without 200 μg/ml silica crystal (purchased from InvivoGen, San Diego, Calif.). The levels of IL-1β (FIG. 3), TNF-α (FIG. 4) and IL-6 (FIG. 5) in the culture medium were measured by ELISA.

Figure 6:
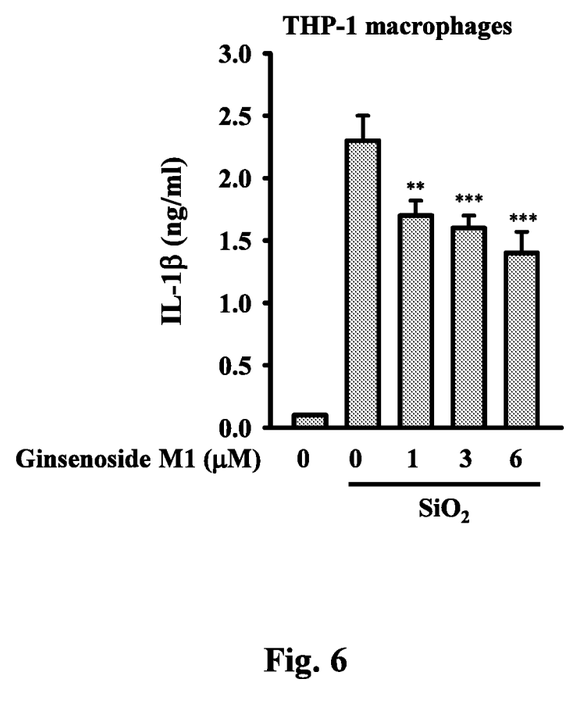
FIG. 6 shows that Human THP-1 macrophages were incubated for 5 h with or without 1 μg/ml LPS, then for 30 min with or without Ginsenoside M1, in the continued presence or absence of LPS, and then for 24 h with or without 200 μg/ml silica crystal. The levels of IL-1β in the culture medium were measured by ELISA.  and * indicates a significant difference at the level of $p<0.01$ and $p<0.001$, respectively compared to silica crystal alone.
Figure 7:
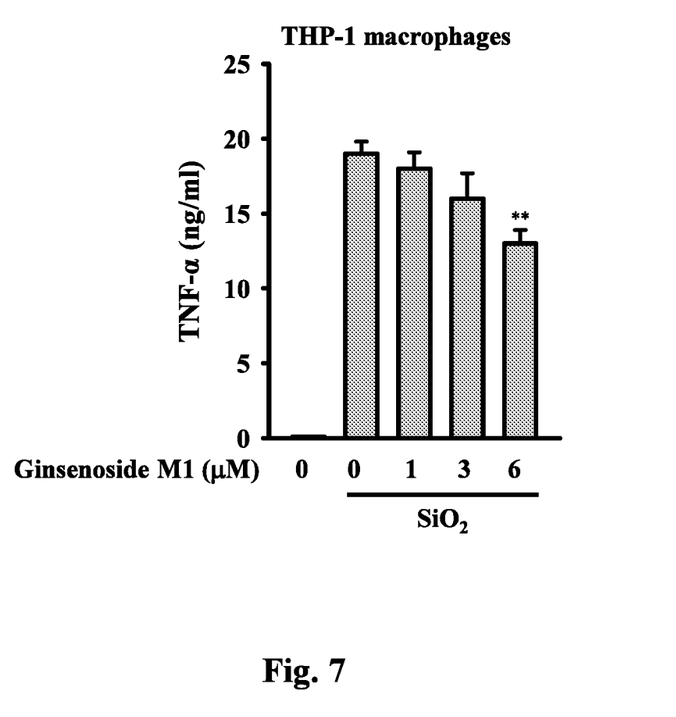
FIG. 7 shows that Human THP-1 macrophages were incubated for 5 h with or without 1 μg/ml LPS, then for 30 min with or without Ginsenoside M1, in the continued presence or absence of LPS, and then for 24 h with or without 200 μg/ml silica crystal. The levels of TNF-α in the culture medium were measured by ELISA. ** indicates a significant difference at the level of $p<0.01$ compared to silica crystal alone.
Figure 8:
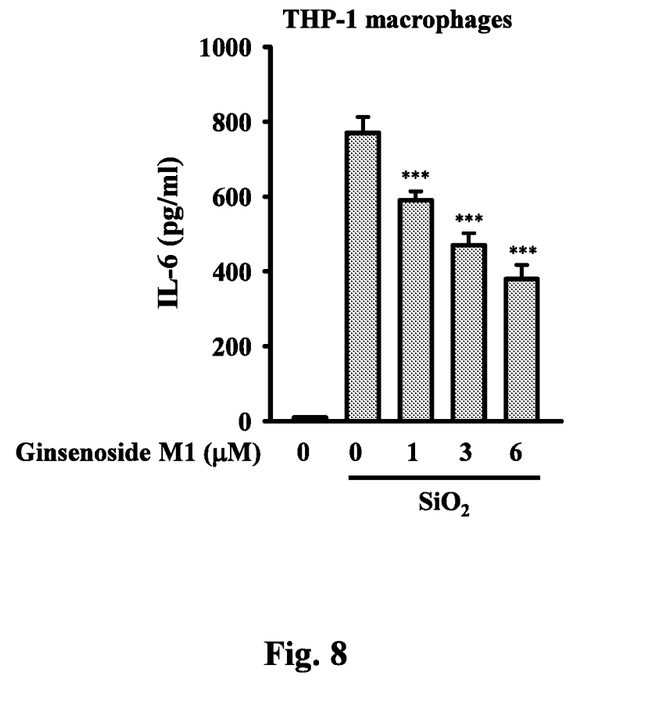
FIG. 8 shows that Human THP-1 macrophages were incubated for 5 h with or without 1 μg/ml LPS, then for 30 min with or without Ginsenoside M1, in the continued presence or absence of LPS, and then for 24 h with or without 200 µg/ml silica crystal. The levels of IL-6 in the culture medium were measured by ELISA. *** indicates a significant difference at the level of p<0.001 compared to silica crystal alone.
Figure 9:
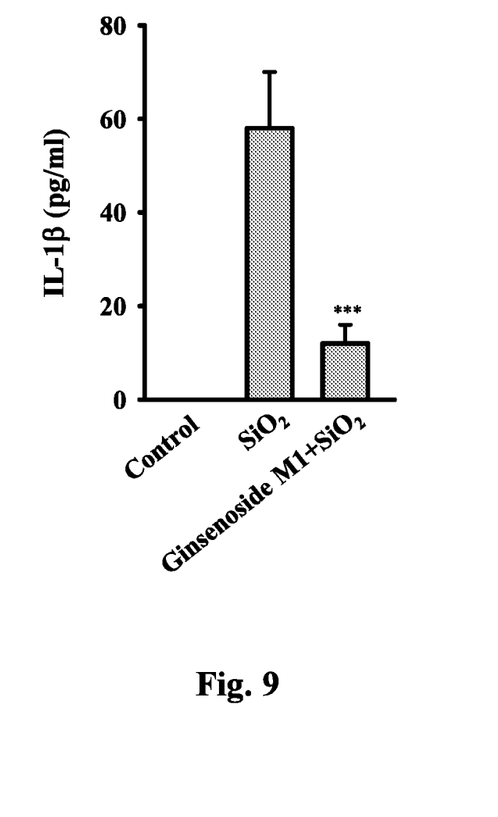
FIG. 9 shows that The levels of IL-1β in the BALF isolated from control mice, silica crystal exposed mice and Ginsenoside M1 oral administered plus silica crystal exposed mice were measured by ELISA. *** indicates a significant difference at the level of p<0.001 compared to silica crystal exposed group.
Figure 10:
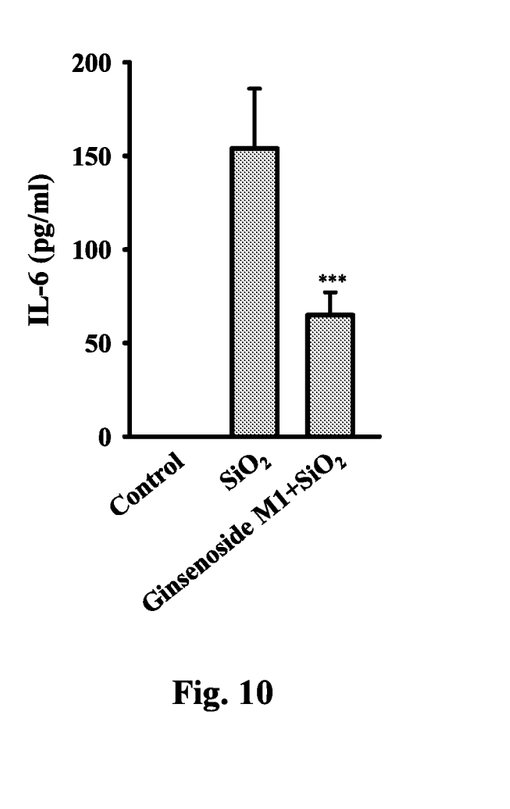
FIG. 10 shows that The levels of IL-6 in the BALF isolated from control mice, silica crystal exposed mice and Ginsenoside M1 oral administered plus silica crystal exposed mice were measured by ELISA. *** indicates a significant difference at the level of p<0.001 compared to silica crystal exposed group.
Figure 11:
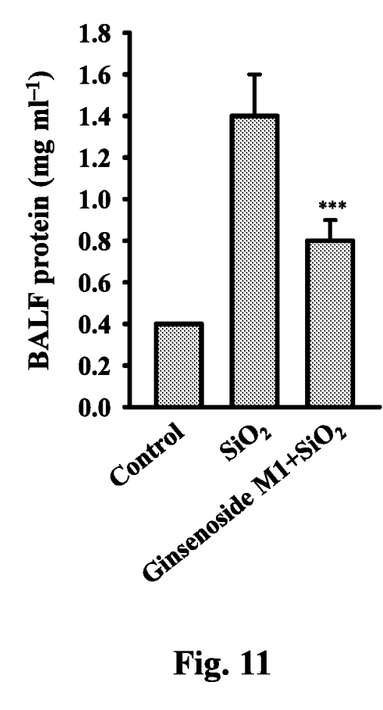
FIG. 11 shows that Total protein concentration in the BALF isolated from control mice, silica crystal exposed mice and Ginsenoside M1 oral administered plus silica crystal exposed mice were measured by protein assay dye. *** indicates a significant difference at the level of p<0.001 compared to silica crystal exposed group.
Figure 12:
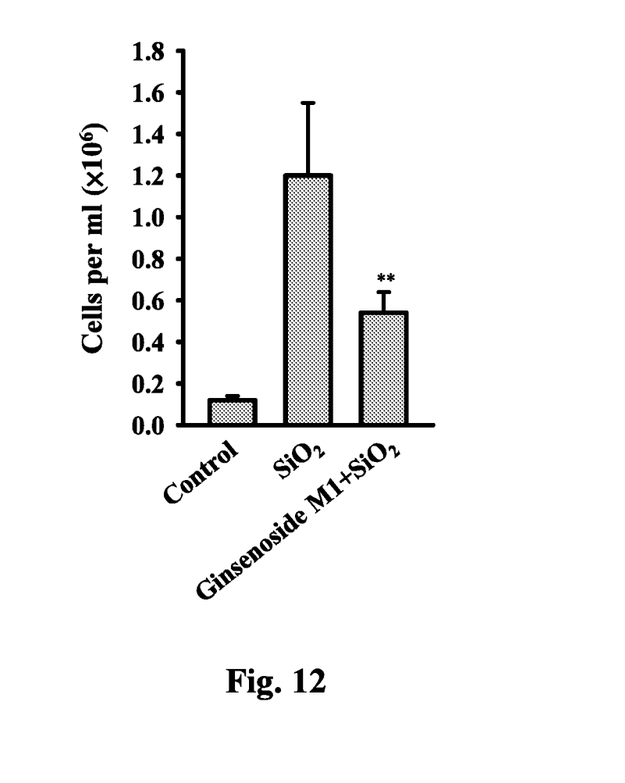
FIG. 12 shows that Total cell number in the BALF isolated from control mice, silica crystal exposed mice and Ginsenoside M1 oral administered plus silica crystal exposed mice were was counted by a hematocytometer. ** indicates a significant difference at the level of p<0.01 compared to silica crystal exposed group.

In FIG. 6-8, THP-1 macrophages ($1\times10^5$ cells/500 μl medium/well) were incubated for 5 h with or without 1 μg/ml LPS, then for 30 min with or without Ginsenoside M1 in the continued presence or absence of LPS, and then for 24 h with or without 200 μg/ml silica crystal. The levels of IL-1β (FIG. 6), TNF-α (FIG. 7) and IL-6 (FIG. 8) in the culture medium were measured by ELISA.

In FIG. 9-12, the animal experiments were conducted in accordance with the guidelines of the National Institutes of Health and approved by the Institutional Animal Care and Use Committee of National Ilan University. Male C57BL/6 mice were purchased from the National Laboratory Animal Center (Taipei, Taiwan). The animals were provided a chow diet and water ad libitum under conditions of 22-24° C., 40-70% relative humidity, and a 12 h light-dark cycle. Ginsenoside M1 (60 mg/kg body weight) was oral administered daily by gavage at day 0, 1 and 2. Silicosis in mice was induced by intratracheally exposed to 40 μl aqueous suspensions of 200 μg of silica crystals in PBS daily at day 0, 1 and 2 (n=6). Each day, mice exposed to silica crystals 4 h after Ginsenoside M1 administration. Control mice received PBS. After 4 h of the last silica crystals exposure, all mice were sacrificed by neck breaking, and a bronchoalveolar lavage was carried out by repeatedly instillating and withdrawing 1 ml of 1% BSA/PBS solution three consecutive times. The levels of IL-1β and IL-6 in the bronchoalveolar lavage fluid (BALF) were measured by ELISA. The total cell number in the BALF was counted by a hematocytometer and protein concentration in the BALF was determined by protein assay dye.

For ELISA assay, 50 μl of biotinylated antibody reagent and 50 μl of culture medium were added to an anti-IL-1β, TNF-α or IL-6 precoated stripwell plate, and incubated at room temperature for 2 h. After washing the plate three times with washing buffer, 100 μl of diluted streptavidin-HRP (horseradish peroxidase) concentrate was added to each well and incubated at room temperature for 30 min. The washing process was repeated; then 100 μl of a premixed tetramethylbenzidine substrate solution was added to each well and developed at room temperature in the dark for 30 min Following the addition of 100 μl of provided stop solution to each well to stop the reaction, the absorbance of the plate was measured by a microplate reader at a 450 nm wavelength.

2. Results 2.1 Ginsenoside M1 Reduces Silica Crystal-Induced IL-1β Production in Mouse J774A.1 Macrophages.

J774A.1 macrophages were incubated for 30 min with or without Ginsenoside M1, then for 5 h with or without 1 μg/ml LPS in the continued presence or absence of Ginsenoside M1, and then for 24 h with or without 200 μg/ml silica crystal. The levels of IL-1β in the culture medium were measured by ELISA. As shown in FIG. 1, the results showed that Ginsenoside M1 reduced IL-1β secretion, indicating that Ginsenoside M1 reduces silicosis-associated inflammation. *** indicates a significant difference at the level of p<0.001 compared to silica crystals alone.

2.2 Ginsenoside M1 Reduces LPS-Induced NLRP3 and proIL-1β Expression in Mouse J774A.1 Macrophages.

J774A.1 macrophages were incubated for 30 min with or without Ginsenoside M1, then for 6 h with or without 1 μg/ml LPS in the continued presence or absence of Ginsenoside M1. The levels of NLRP3 and proIL-1β in the cell lysates were measured by Western blot. As shown in FIG. 2, the results showed that Ginsenoside M1 reduced the levels of NLRP3 and proIL-1β in LPS-activated J774A.1 macrophages.

In summary, our study shows that Ginsenoside M1 is effective in reducing silica crystal-induced IL-1β production (FIG. 1) and LPS-induced NLRP3 and proIL-1β expression (FIG. 2) in macrophages. These findings indicate that Ginsenoside M1 is effective in preventing and mitigating silicosis.

2.3 Ginsenoside M1 Reduces Silica Crystal-Induced IL-1β, TNF-α and IL-6 Production in THP-1 Macrophages.

To confirm the anti-inflammatory activities of Ginsenoside M1, human THP-1 macrophages were incubated for 30 min with or without Ginsenoside M1, then for 5 h with or without 1 μg/ml LPS in the continued presence or absence of Ginsenoside M1, and then for 24 h with or without 200 μg/ml silica crystal. The levels of IL-1β, TNF-α and IL-6 in the culture medium were measured by ELISA. As shown in FIG. 3-5, the results showed that Ginsenoside M1 reduced IL-1β production (FIG. 3), TNF-α production (FIG. 4) and IL-6 production (FIG. 5), indicating that Ginsenoside M1 reduces silicosis-associated inflammation in human macrophage. *,  and * indicates a significant difference at the level of p<0.05, p<0.01 and p<0.001, respectively compared to silica crystals alone.

2.4 Ginsenoside M1 Reduces Silica Crystal-Induced IL-1β, TNF-α and IL-6 Production in LPS-Primed THP-1 Macrophages.

To investigate whether Ginsenoside M1 inhibits silica crystal-mediated activation signaling of NLRP3 inflammasome, human THP-1 macrophages were primed for 5 h min with or without 1 µg/ml LPS, then for 30 min with or without Ginsenoside M1 in the continued presence or absence of LPS, and then for 24 h with or without 200 µg/ml silica crystal. The levels of IL-1β, TNF-α and IL-6 in the culture medium were measured by ELISA. As shown in FIG. 6-8, the results showed that Ginsenoside M1 reduced IL-1β production (FIG. 6), TNF-α production (FIG. 7) and IL-6 production (FIG. 8) in LPS-primed THP-1 macrophages, indicating that Ginsenoside M1 reduces silicosis-associated inflammation in human macrophage through inhibiting the activation signal of NLRP3 inflammasome.  and * indicates a significant difference at the level of p<0.01 and p<0.001, respectively compared to silica crystals alone.

2.5 Ginsenoside M1 Reduces Silica Crystal-Induced Silicosis In Vivo.

Mice intratracheally exposed to silica crystal significantly increased IL-1β (FIG. 9) and IL-6 (FIG. 10) production in the murine BALF compared with the control mice. The oral administration of Ginsenoside M1 significantly reduced silica crystal-induced IL-1β (FIG. 9) and IL-6 (FIG. 10) production in the murine BALF. Silica crystal also significantly increased the total protein concentration (FIG. 11) and total cell number (FIG. 12) in BALF, and these effects were significantly inhibited by Ginsenoside M1.

It is believed that a person of ordinary knowledge in the art where the present invention belongs can utilize the present invention to its broadest scope based on the descriptions herein with no need of further illustration. Therefore, the descriptions and claims as provided should be understood as of demonstrative purpose instead of limitative in any way to the scope of the present invention.

REFERENCES

Cassel S L, Joly S, Sutterwala F S. 2009. The NLRP3 inflammasome: a sensor of immune danger signals. Semin Immunol 21(4): 194-198.

Davis B K, Wen H, Ting J P. 2011. The inflammasome NLRs in immunity, inflammation, and associated diseases. Annu Rev Immunol 29: 707-735.

Duewell P, Kono H, Rayner K J, Sirois C M, Vladimer G, Bauernfeind F G, Abela G S, Franchi L, Nuñez G, Schnurr M, Espevik T, Lien E, Fitzgerald K A, Rock K L, Moore K J, Wright S Df, Hornung V, Latz E. 2010. NLRP3 inflammasomes are required for atherogenesis and activated by cholesterol crystals. Nature 464:1357-1361.

Hornung V, Bauernfeind F, Halle A, Samstad E O, Kono H, Rock K L, Fitzgerald K A, Latz E. 2008. Silica crystals and aluminum salts activate the NALP3 inflammasome through phagosomal destabilization. Nat Immunol 9(8): 847-856.

Hsu H Y, Wen M H. 2002. Lipopolysaccharide-mediated reactive oxygen species and signal transduction in the regulation of interleukin-1 gene expression. J Biol Chem 277(25): 22131-22139.

Huaux F. 2007. New developments in the understanding of immunology in silicosis. Current opinion in allergy and clinical immunology 7: 168-173.

Jin C, Flavell R A. 2010. Molecular mechanism of NLRP3 inflammasome activation. J Clin Immunol 30(5): 628-631.

Martinon F, Mayor A, Tschopp J. 2009. The inflammasomes: guardians of the body. Annu Rev Immunol 27: 229-265.

Miller D K, Myerson J, Becker J W. 1997. The interleukin-1 beta converting enzyme family of cysteine proteases. J Cell Biochem 64(1): 2-10.

Peeters P M, Eurlings I M, Perkins T N, Wouters E F, Schins R P, Borm P J, Drommer W, Reynaert N L, Albrecht C. 2014. Silica-induced NLRP3 inflammasome activation in vitro and in rat lungs. Part Fibre Toxicol 11(1): 58.

Schroder K, Tschopp J. 2010. The inflammasomes. Cell 140(6): 821-832.

We claim:

1. A method of treating silicosis in a subject in need thereof comprising administering to the subject an amount of ginsenoside M1 effective to treat the subject.

2. The method of claim 1, wherein the method of treating is effective in inhibiting silica crystal-induced activation of NLRP3 inflammasome.

3. The method of claim 1, wherein the method of treating is effective in inhibiting silica crystal-induced interleukin 1β production through NLRP3 inflammasome.

4. The method of claim 1, wherein the ginsenoside M1 is administered by parenteral or enteral route.

* * * * *